US008903474B2

(12) United States Patent
Yaniv et al.

(10) Patent No.: US 8,903,474 B2
(45) Date of Patent: Dec. 2, 2014

(54) ANALYSIS OF GASES

(75) Inventors: Zvi Yaniv, Austin, TX (US); Prabhu Soundarrajan, Austin, TX (US)

(73) Assignee: PEN Inc., Deerfield Beach, FL (US)

( * ) Notice: Subject to any disclaimer, the term of this patent is extended or adjusted under 35 U.S.C. 154(b) by 1899 days.

(21) Appl. No.: 11/566,919

(22) Filed: Dec. 5, 2006

(65) Prior Publication Data

US 2007/0167832 A1    Jul. 19, 2007

Related U.S. Application Data

(60) Provisional application No. 60/742,580, filed on Dec. 6, 2005.

(51) Int. Cl.
*A61B 6/00* (2006.01)
*A61B 5/1455* (2006.01)

(52) U.S. Cl.
CPC .... *A61B 5/14551* (2013.01); *G01N 2291/0427* (2013.01)
USPC .......................................................... 600/475

(58) Field of Classification Search
None
See application file for complete search history.

(56) References Cited

U.S. PATENT DOCUMENTS

| | | | |
|---|---|---|---|
| 3,791,200 | A | 2/1974 | Hayre |
| 4,150,561 | A | 4/1979 | Zupanick |
| 4,150,670 | A | 4/1979 | Jewett et al. |
| 4,847,783 | A | 7/1989 | Grace et al. |
| 4,907,441 | A | 3/1990 | Shurmer |
| 5,042,501 | A | 8/1991 | Kenny et al. |
| 5,076,094 | A | 12/1991 | Frye et al. |
| 5,325,704 | A | 7/1994 | Mariani et al. |
| 5,461,562 | A | 10/1995 | Tabanou et al. |
| 5,469,369 | A | 11/1995 | Rose-Pehrsson et al. |
| 5,971,934 | A | 10/1999 | Scherer et al. |
| 6,363,772 | B1 * | 4/2002 | Berry ............................ 73/24.02 |
| 6,599,253 | B1 | 7/2003 | Baum et al. |
| 2001/0037070 | A1 | 11/2001 | Cranley et al. |
| 2003/0134433 | A1 | 7/2003 | Gabriel et al. |
| 2004/0082872 | A1 | 4/2004 | von Bahr et al. |
| 2004/0261500 | A1 | 12/2004 | Ng et al. |

FOREIGN PATENT DOCUMENTS

| | | |
|---|---|---|
| CN | 1681435 A | 10/2005 |
| EP | 1102200 | 5/2001 |
| EP | 1976431 B1 | 5/2011 |
| JP | 10000186 | 1/1998 |
| JP | 10248826 | 9/1998 |
| JP | 2002-518668 | 6/2002 |
| JP | 2004-081854 | 3/2004 |
| JP | 2004-508534 | 3/2004 |
| JP | 2005-501233 | 1/2005 |
| WO | WO 00/50890 | 8/2000 |
| WO | WO 01/63277 | 8/2001 |
| WO | WO2006/018237 A1 | 2/2006 |
| WO | WO 2006/018237 A1 | 2/2006 |

OTHER PUBLICATIONS

Von Basum et al. Online recording of ethane traces in human breath via infrared laser spectroscopy. Journal of Applied Physiology 2003, vol. 95, pp. 2583-2590.*
Harren et al. On-line laser photoacoustic detection of ethene in exhaled air as biomarker of ultraviolet radiation damage of the human skin. Applied Physics Letter 1999, vol. 74, No. 12, pp. 1761-1763.*
Paredi et al. Elevation of Exhaled Ethane Concentration in Asthma. American Journal of Respiratory Critical Care Medicine 2000, vol. 162, pp. 1450-1454.*
Giubileo, Gianfranco. Medical diagnostics by laser-based analysis of exhaled breath. SPIE Proceedings 2002, vol. 4762, pp. 318-325.*
Casellas, et al., "Hydrogen breath test with glucose in exocrine pancreatic insufficiency", *Pancreas*, May 1998, 16 (4): pp. 481-486, www.pubmed.gov (PMID: 9598808), Digestive System Research Unit, Hospital General Vall d'Hebron, Barcelona, Spain, retrieved Apr. 2, 2007 from www.ncbi.nlm.nih.gov.
Handleman, et al., "Breath Ethane in Dialysis Patients and Control Subjects", *Free Radic Biol Med.*, Jul. 1, 2003; 35(1): pp. 17-23, www.pubmed.gov (PMID: 12826252), National Library of Medicine and the National Institute of Health, US, retrieved Apr. 2, 2007 from www.ncbi.nlm.nih.gov.
PCT/US06/61674 International Search Report and Written Opinion, PCT, Feb. 13, 2008.
Hou, Zhongyu et al.; Application of Carbon Nanotubes to Human Breath Dynamics Characterization; *Applied Physics Letters*; vol. 89, No. 053105, pp. 1-3, 2006.
Office Action, Notice of Reasons for Rejection, Japanese Application No, 2008-544640, Nov. 15, 2011.
Supplementary European Search Report, Application No. EP06846500, Sep. 29, 2009.
European Office Action, Application No. 06846500.4, Jun. 14, 2010.
Basum et al,, "Online recording of ethane traces in human breath via infrared laser spectroscopy," Innovative Methodology, J. Appl. Physiol 95; pp. 2583-2590, Aug. 1, 2003.
Harren et al., "On-line laser photoacoustic detection of ethane in exhaled air as biomarker of ultraviolet radiation damage of the human skin," Appl. Phys. Lett. 74, pp. 1761-1763, Mar. 22, 1999.

(Continued)

*Primary Examiner* — Louise Humphrey
(74) *Attorney, Agent, or Firm* — Kelly Kordzik; Matheson Keys & Kordzik PLLC

(57) ABSTRACT

Systems and techniques for the analysis of gases for medical purposes are described. In one aspect, a system includes a sample collector to collect a physical sample associated with an individual and present a gas sample for analysis, a gas analysis device to analyze the gas sample presented by the sample collector to determine a concentration of one or more non-aqueous gases in the gas sample, a data storage device that includes information reflecting a correlation between concentration of the one or more non-aqueous gases in the gas sample and a disease state, and a data analysis device to determine a medical condition of the individual based on the concentration of one or more non-aqueous gases in the gas sample and the information.

22 Claims, 8 Drawing Sheets

(56) References Cited

OTHER PUBLICATIONS

Japanese Patent Office, Office Action, Decision of Rejection, Japanese Application No. 2008-544640, Dec. 4, 2012.

TIPLO, Taiwan IPO Search Report, Taiwan Invention Patent Application No. 095145459, dated Jan. 16, 2013.

TIPLO, Translation of Notification and Taiwan IPO Search Report, Application No. 095145459, dated Jun. 13, 2012.

Hou et al., "Application of Carbon Nanotubes to Human Breath Dynamics Characterization", *Applied Physics Letters*, Jul. 31, 2006, 89, 053105 (2006): pp. 053105-1 through 053105-3, American Institute of Physics.

Mansfield, et al., "The Application of Infrared Spectroscopy to Breath $CO_2$ Isotope Ratio Measurements and the Risk of Spurious Results", *Phys. Med. Biol.*, Nov. 24, 1997, vol. 43 (1998): pp. 1225-1239, Infrared Science and Technology Group, Electronics & Computer Science Department, University of Southampton, Southampton SO17 1BJ, UK.

None, "FDA Clears New Breath Test for Monitoring Asthma", *Lab Tests Online*, May 1, 2003, American Association for Clinical Chemistry, retrieved Apr. 2, 2007 from http://www.labtestsonline.org/news/fdaasthma030509.html.

None, "*Helicobacter pylori*", *Lab Tests Online*, Jun. 24, 2005, American Association for Clinical Chemistry, retrieved Apr. 2, 2007 from http://www.labtestsonline.org/understanding/analyics/h_pylori/multiprint.html.

None, "Trace Gas Release and human health", "UV-radiation damage", "Other applications to human health and medicine", *Human Health*, Jan. 11, 2000, retrieved Apr. 2, 2007 from www.tracegasfac.science.ru.nl/respirat1.htm.

Pavlou, et al., "Sniffing Out the Truth: Clinical Diagnosis Using the Electronics Nose", *Clin. Chem. Lab. Med. 2000*, 38(2): 99-112, Walter de Gruyter—Berlin—New York.

Ritter, Steve, "New Car Smell", *Science and Technology*, May 20, 2002, vol. 80, No. 20, CENEAR 80 20 p. 45, ISSN 0009-2347, American Chemical Society.

Simenhoff, et al., "Biochemical Profile of Uremic Breath", *The New England Journal of Medicine*, Jul. 21, 1997; pp. 132-135, Massachusetts Medical Society—Registry on Continuing Medical Education, Boston, MA; US.

Wood, Lindsay, "Some buildings could be hazardous to your health", *The Galt Global Review*, Sep. 15, 2005, Galt Western Personnel Ltd. (galtglobalreview.com).

* cited by examiner

| INDIVIDUAL AB ||||
|---|---|---|
| COMPONENTS | CHARACTERISTIC 1 | CHARACTERISTIC 2 |
| COMPONENT 1 | 44 | 2 |
| COMPONENT 2 | 55 | 1 |
| ... | ... | ... |
| COMPONENT N | 66 | 0 |

ANALYSIS OF GASES

CROSS-REFERENCE TO RELATED APPLICATIONS

This application claims the priority of U.S. Provisional Application Ser. No. 60/742,580, filed on Dec. 6, 2005, the contents of which are incorporated herein by reference.

BACKGROUND

This disclosure relates generally to the analysis of gases, and more particularly to the analysis of gases for medical monitoring and diagnosis.

DESCRIPTION OF DRAWINGS

Like reference symbols in the various drawings indicate like elements.

DETAILED DESCRIPTION

Figure 1:
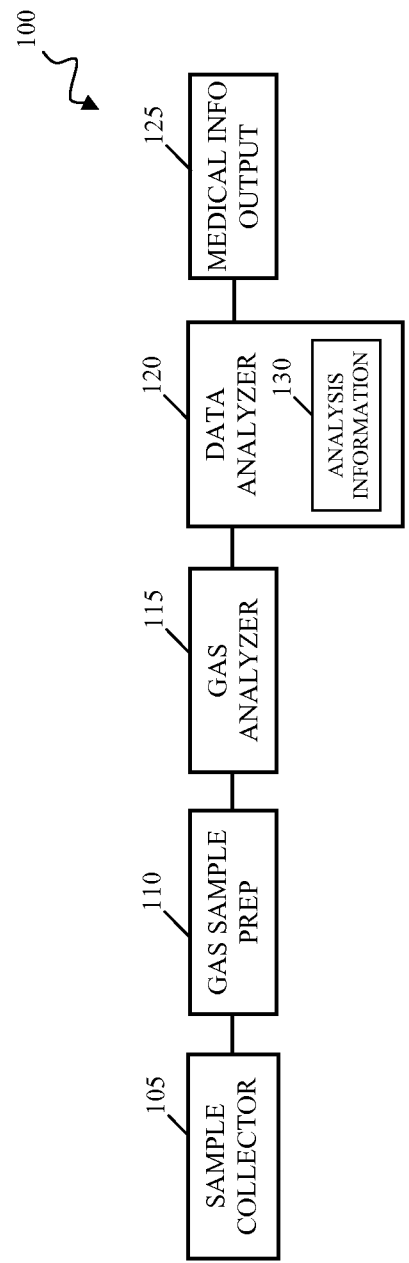
FIG. 1 is a schematic representation of a system for the analysis of gases in accordance with one implementation of the invention.

FIG. 1 is a schematic representation of a system 100 for the analysis of gases, such as for medical analysis. System 100 includes a sample collector 105, a gas sample preparation device 110, a gas analyzer 115, a data analyzer 120, and an output 125 that cooperate in the analysis of gases for medical purposes such as medical monitoring and diagnosis.

Sample collector 105 is a device for collecting a sample that is relevant to the analysis of a gas. The sample may be a solid sample, a liquid sample, or a gaseous sample. The design and structure of sample collector 105 may reflect the nature of the sample to be collected. For example, when gaseous samples such as breath are collected, sample collector 105 may include a balloon or other concentrator. As another example, when liquid samples such as urine, blood, sweat, or saliva are collected, sample collector 105 may include a bowl, a capillary tube, or other receptacle that is suitable for collecting a liquid. As yet another example, when solid samples such as feces or tissue are collected, sample collector 105 may include a plate, a sheet, or other receptacle that is suitable for collecting a solid.

Sample collector 105 may also include one or more devices for conveying a collected sample to gas sample preparation device 110. The design and structure of such conveyance devices may reflect the nature of the collected sample. Examples of conveyance devices include pumps, valves, conveyor belts, and the like.

In some implementations, sample collector 105 may also include one or more data outputs and inputs for exchanging information with other components of system 100. For example, sample collector 105 may include a level indication output that may be used to signal other components in system 100 that an amount of sample has been collected. As another example, sample collector 105 may include a control signal input that receives control signals from other components in system 100. The control signals may, e.g., trigger the start or end of sample collection, change sample collection parameters, or the like. As yet another example, sample collector 105 may include a measurement output that outputs information characterizing the collection of a sample by sample collector 105. For example, the measurement output may characterize the number of breaths by an individual that were collected Gas sample preparation device 110 is a device for preparing a gaseous sample from the sample collected by collector 105. The preparations provided by sample preparation device 110 may include evaporation of liquid samples, particulate removal, dehumidification, sample concentration, and the like. Sample preparation device 110 may thus include one or more evaporators (such as a heater or depressurizing chamber), particulate removal devices (such as an aerosol filter, an impactor, an electrostatic precipitator, or the like), one or more dehumidifying elements (such as a condenser, humidity scavengers, or the like), or one or more concentrators (such as activated carbon, cooled physisorption elements, and the like).

The design and structure of gas sample preparation device 110 may reflect the nature of the sample collected by sample collector 105. For example, when solid and liquid samples are collected, gas sample preparation device 10 may include an evacuator, a heater, or other device for gasifying a solid or a liquid sample.

In some implementations, sample preparation device 110 may also include one or more data outputs and inputs for exchanging information with other components of system 100. For example, sample preparation device 110 may include a level indication output that may be used to signal other components in system 100 that an amount of sample has been prepared. As another example, sample preparation device 110 may include a control signal input that receives control signals from other components in system 100. The control signals may, e.g., trigger the start or end of sample preparation, change sample preparation parameters, or the like. As yet another example, sample preparation device 110 may include a measurement output that outputs information characterizing the preparation of a sample by sample preparation device 110. For example, the measurement output may characterize the amount of humidity removed from a sample, the operational parameters of active elements such as condensers, and the like. As yet another example, sample preparation device 110 may include a control signal output that generates control signals directed other components in system 100. The control signals may, e.g., trigger the start or end of sample collection, change sample collection parameters, or the like.

Gas analyzer 115 is a device for analyzing a gaseous sample prepared by gas sample preparation device 110 to generate one or more signals that characterize the gaseous sample. Gas analyzer 115 may analyze a gaseous sample by measuring one or more characteristics of the gaseous sample, including the sample's physical, optical, and chemical properties. For example, gas analyzer may determine the concentration of one or more constituent gas species in a gaseous sample. The constituent gas species may include species other than water, i.e., the species may be non-aqueous. For example, when the gaseous sample is breath, the constituent gas species may be breath trace compounds.

Gas analyzer 115 may include one or more optical spectroscopy devices, such as infrared spectroscopy devices. In one implementation, gas analyzer 115 may include a photoacoustic spectrometer, as discussed further below.

In some implementations, gas analyzer 115 may also include one or more data outputs and inputs for exchanging information with other components of system 100. For example, gas analyzer 115 may include a control signal input that receives control signals from other components in system 100. The control signals may, e.g., trigger the start or end of gas analysis, change gas analysis parameters, or the like. As yet another example, gas analyzer 115 may include a measurement output that outputs measurement information characterizing a gas sample. Note that such measurement information may be output to multiple components in system 100 (i.e., in addition to the output to data analyzer 120). Such measurement information may be used by other components in the control of their operations. Alternatively, gas analyzer 115 may include one or more control signal outputs that provide one or more control signals directly to one or more other components.

Data analyzer 120 is a device for analyzing the characterization of the gaseous sample by gas analyzer 115, such as, e.g., to characterize a medical condition of an individual associated with the characterized gaseous sample. The medical condition characterization may be used for purposes such as medical monitoring and diagnosis. In some implementations, the analysis of the characterization may be used for other purposes, such as environmental monitoring and the like. Data analyzer 120 may include a data processing device that performs data processing activities in accordance with the logic of a set of machine-readable instructions. Such instructions may be tangibly embodied in a variety of information carriers, including hardware (such as ASIC's and/or other circuitry) and/or software (stored on devices such as hard drives, compact discs, memory cards, or the like).

The data processing activities performed by data analyzer 120 may include statistical analysis of the likelihood that the concentration of a species in a gaseous sample has changed. In some implementations, such a change may also be associated with an analysis of the likelihood that a disease state is present in an individual. The statistical analysis may include any of a number of different statistical approaches, including traditional statistical tests, pattern recognition, fuzzy logic, rule-based expert systems, and the like. Data analyzer 120 may thus include a neural network, a data processing device that performs activities embodying a principal component analysis model, or the like.

The statistical analyses performed by data analyzer 120 may be based on a set of analysis information 130 that is accessible to data analyzer 120 . Analysis information 130 is a collection of information that may be used to determine a correlation between the characterization of a gaseous sample by gas analyzer 115 and a disease state. Analysis information 130 may be stored locally or remotely, in software or in hardware. In some implementations, analysis information 130 may be dynamically changeable to reflect an updated understanding of the disposition of an individual and/or the components of system 100.

In some implementations, data analyzer 120 may also include one or more data outputs and inputs for exchanging information with other components of system 100. For example, data analyzer 120 may include a control signal input that receives control signals from other components in system 100. The control signals may, e.g., trigger the start or end of data analysis, change data analysis parameters, or the like. As yet another example, data analyzer 120 may include an analysis output that outputs a characterization of a medical parameter. Note that such a medical parameter characterization may be output to multiple components in system 100 (i.e., in addition to the output to medical information output 125). Such a medical parameter characterization may be used as a control signal at other components. Alternatively, data analyzer 120 may include one or more control signal outputs that provide one or more control signals to one or more other components.

The components of system 100 may be arranged in different ways and yet still cooperate in the analysis of gases. For example, in some implementations, system 100 may be a handheld or other patient-portable device that may be carried by an individual. In other implementations, components of system 100 may be remote from one another and connected using a data communications network, such as the Internet.

Figure 2:
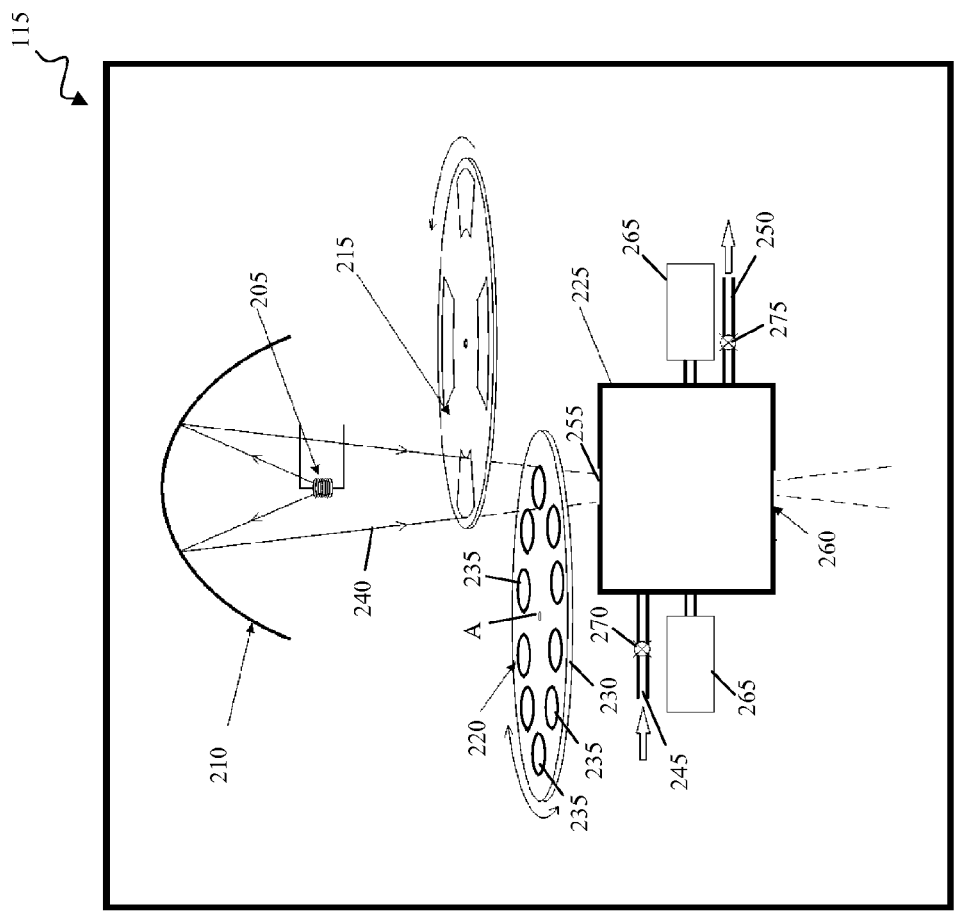
FIG. 2 is a schematic representation of a gas analyzer that may be included in the system of FIG. 1.

FIG. 2 is a schematic representation of a gas analyzer 115 that may be included in system 100 (FIG. 1). Gas analyzer 115 includes an electromagnetic radiation source 205, an electromagnetic radiation collector 210, a timing device 215, a wavelength selection device 220, and an analysis chamber 225.

Electromagnetic radiation source 205 is a source of electromagnetic radiation, such as infrared radiation. At least some of the electromagnetic radiation generated by source 205 is of a wavelength that may interact with one or more potential constituents of an analyzed gas. For example, source 205 can emit near, middle, far, or THz frequency infrared radiation. Source 205 may be a relatively broadband source, such as a hot wire filament of an incandescent bulb. In other implementations, source 205 may be a relatively narrowband source, such as a light emitting diode or laser source (not shown). In some implementations, source 205 may include multiple, discrete elements. For example, source 205 may include an array of LED's that emit in the infrared, e.g., at 4.3, 4.7, 3.4, and 2.7 micrometers.

Electromagnetic radiation collector 210 is a device to collect at least some of the electromagnetic radiation generated by source 205. Collector 210 may be a parabolic or spherical mirror. Collector 210 may also be a lens or a combination of these and other optical elements. For example, collector 210 may include a collimator, a ZnSe lens, or the like.

Timing device 215 is a device that varies the incidence of the electromagnetic radiation on analysis chamber 225 with time. For example, timing device 215 may be a chopper wheel, as shown. In other implementations, timing device 215 may be a different mechanical device (such as a rotating mirror or a shutter) or an electrical device (such as a oscillator or switch that varies the generation of electromagnetic radiation by source 205). In some implementations, timing device 215 may be an aspect of source 205, such as when source 205 is a pulsed laser source.

Wavelength selection device 220 is a device that varies the wavelength of the electromagnetic radiation incident on analysis chamber 225. For example, wavelength selection device 220 may be a wheel 230 that includes a collection of filter windows 235 that each transmit electromagnetic radiation of selected wavelengths. Wheel 230 is rotatable about an axis A and is positioned to intersect an optical path 240 for the transmission of electromagnetic radiation from collector 210 to analysis chamber 225. Filter windows 235 may be positioned in a circle around axis A so that the rotation of wheel 230 about axis A sequentially moves different filter windows 235 across the intersection of wheel 230 and optical path 240. During rotation, as optical path 240 intersects this series of windows 235, the wavelength of radiation incident on analysis chamber 225 will vary in accordance with the transmission spectra of windows 235.

Wavelength selection device 220 may be implemented in other ways. For example, mirrors may be used instead of transmission filters, and the mechanics of insertion in optical path 240 may be changed. In some implementations, wavelength selection device 220 may be an aspect of source 205, such as when source 205 is a tunable laser source.

Analysis chamber 225 is an enclosure that contains a gaseous sample and presents it for interaction with at least some of the electromagnetic radiation generated by source 205. As shown, analysis chamber 225 includes a sample inlet 245, a sample outlet 250, an electromagnetic radiation inlet 255, an electromagnetic radiation sink 260, and one or more transducers 265.

Sample inlet 245 may include a tube that creates a fluid flow path from gas sample preparation device 110 (FIG. 1) to analysis chamber 225 for the transport of a gas sample. Sample inlet 245 may include a valve 270 or other flow regulator to control the transport of the gas sample to analysis chamber 225. Sample outlet 250 creates a fluid flow path to release a gas sample from analysis chamber 225. Sample outlet 250 may include a valve 275 or other flow regulator to control the transport of the gas sample from analysis chamber 225. In some implementations, valves 270, 275 may be operated automatically to control the residence time of a sample in analysis chamber 225.

Electromagnetic radiation inlet 255 is a window that passes at least some of the electromagnetic radiation generated by source 205 into analysis chamber 225 but yet assists in the containment of a gaseous sample. For example, electromagnetic radiation inlet 255 may be a germanium window. Electromagnetic radiation sink 260 is a device that decreases the amount of electromagnetic radiation in analysis chamber 225 but yet assists in the containment of a gaseous sample. For example, electromagnetic radiation sink 260 may be a germanium window to allow electromagnetic radiation to pass out of analysis chamber 225, as shown. In other implementations, electromagnetic radiation sink 260 may be a black body or other absorber of electromagnetic radiation.

Transducers 265 are one or more devices that convert the interaction of electromagnetic radiation with a gaseous sample in analysis chamber 225 into an electrical signal. For example, transducers 265 may be acoustic transducers (such as microphones, cantilever elements, or other acoustic detectors) that sense sound generated by the interaction of infrared electromagnetic radiation with a gaseous sample for the performance of photoacoustic spectroscopy, as shown. For example, transducers 265 may be ½" condenser free-field Sennheiser ME66 microphones (Sennheiser Electronic Corporation, Old Lyme, Conn.).

In other implementations, transducers 265 may sense the interaction of electromagnetic radiation with a gaseous sample in other ways. For example, transducers 265 may be photodetectors that measure the transmission spectra of electromagnetic radiation across analysis chamber 225.

Figure 3:
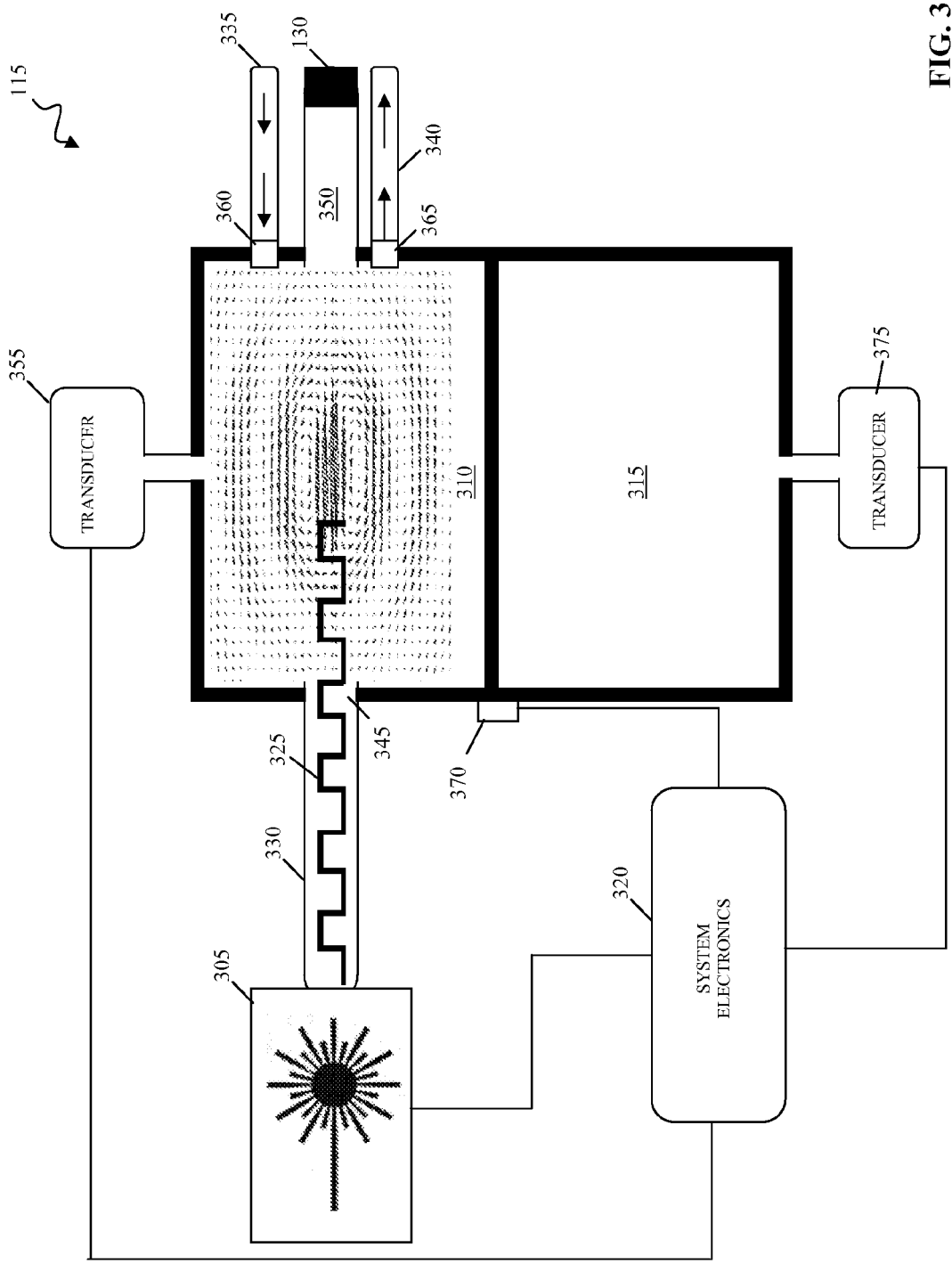
FIG. 3 is a schematic representation of another gas analyzer that may be included in the system of FIG. 1.

FIG. 3 is a schematic representation of an alternative gas analyzer 115 that may be included in system 100 (FIG. 1). Gas analyzer 115 includes an electromagnetic radiation source 305, a measurement chamber 310, a reference chamber 315, and a collection of system electronics 320.

Electromagnetic radiation source 305 is a source of electromagnetic radiation, such a pulsed diode laser as shown. A pulsed diode laser may generate a pulsed beam of electromagnetic radiation 320 that propagates along a path 330 to measurement chamber 310. In some implementations, path 330 may be a waveguide. In some implementations, electromagnetic radiation source 305 may be tunable to generate electromagnetic radiation of various wavelengths.

Measurement chamber 310 is an enclosure that may contain a gaseous sample and present it for interaction with at least some of the electromagnetic radiation generated by source 205. As shown, measurement chamber 310 includes a sample inlet 335, a sample outlet 340, an electromagnetic radiation inlet 345, an electromagnetic radiation sink 350, and one or more transducers 355. Sample inlet 335 may include a tube that creates a fluid flow path from gas sample preparation device 110 (FIG. 1) to measurement chamber 310 for the transport of a gas sample. Sample inlet 335 may include an acoustic dampener 360 or other mechanism to hinder or prevent the transmission of sound into measurement chamber 310 along with a gas sample. Sample outlet 340 creates a fluid flow path to release a gas sample from measurement chamber 310. Sample outlet 340 may include an acoustic dampener 365 or other mechanism to hinder or prevent the transmission of sound into measurement chamber 310 along the fluid flow path of sample outlet 340.

Electromagnetic radiation inlet 345 is a window that passes at least some of the electromagnetic radiation generated by source 305 into measurement chamber 310 but yet assists in the containment of a gaseous sample. For example, electromagnetic radiation inlet 345 may be a germanium window. Electromagnetic radiation sink 350 is a device that decreases the amount of electromagnetic radiation in measurement chamber 310 but yet assists in the containment of a gaseous sample. For example, electromagnetic radiation sink 350 may be a beam dump.

Transducers 355 are one or more devices that convert acoustic energy resulting from the interaction of an infrared electromagnetic radiation with a gaseous sample in measurement chamber 310 into an electrical signal. For example, transducers 355 may be one or more microphones, cantilevered elements, or the like for the performance of photoacoustic spectroscopy.

Reference chamber 315 is an enclosure that contains a reference gas sample that mimics at least some of the properties of a gaseous sample in measurement chamber 310. The reference sample in reference chamber 315 may mimic the gaseous sample in measurement chamber 310 by having a pressure, temperature, or even composition that is comparable to that expected of the gaseous sample in measurement chamber 310. Such mimicry may be obtained using active and/or passive elements. For example, comparable temperatures may be obtained by passive thermal coupling of reference chamber 315 and measurement chamber 310. As another example, reference chamber 315 and/or measurement chamber 310 may include active elements, such as heaters or coolers, to maintain comparable temperatures. In either case, information regarding the temperature and/or pressure of reference chamber 315 and measurement chamber 310 may be obtained using one or more sensors 370 that provide measurement results or other information to system electronics 320.

In contrast with measurement chamber 310, reference chamber 315 isolates the reference gaseous sample from interaction with the electromagnetic radiation generated by source 305. Reference chamber 315 may also include one or more transducers 375 that convert background acoustic energy of the gaseous sample in reference chamber 315 into an electrical signal. Since reference chamber 315 isolates the reference sample from interaction with the electromagnetic radiation generated by source 205, such background acoustic energy does not result from interaction with this electromagnetic radiation. Instead, such background acoustic energy represents noise. Thus, reference chamber 315 may allow differential measurements to be made and the consequences of interaction between gaseous sample in measurement chamber 310 and electromagnetic radiation to be resolved more easily.

System electronics 320 is a collection of circuitry for controlling and analyzing the analysis of gaseous samples by gas analyzer 115. For example, system electronics 320 may include inputs to receive measurement results from transducers 355, 375 and sensors 370. System electronics 320 may also include one or more control signal outputs, such as a signal output that controls the pulsing and/or wavelength of light generated by source 305. As other examples, system electronics 320 may also include signal outputs that control valves on inlet 335 and outlet 340, active temperature and pressure control elements associated with chambers 310, 315, and the like.

Figure 4:
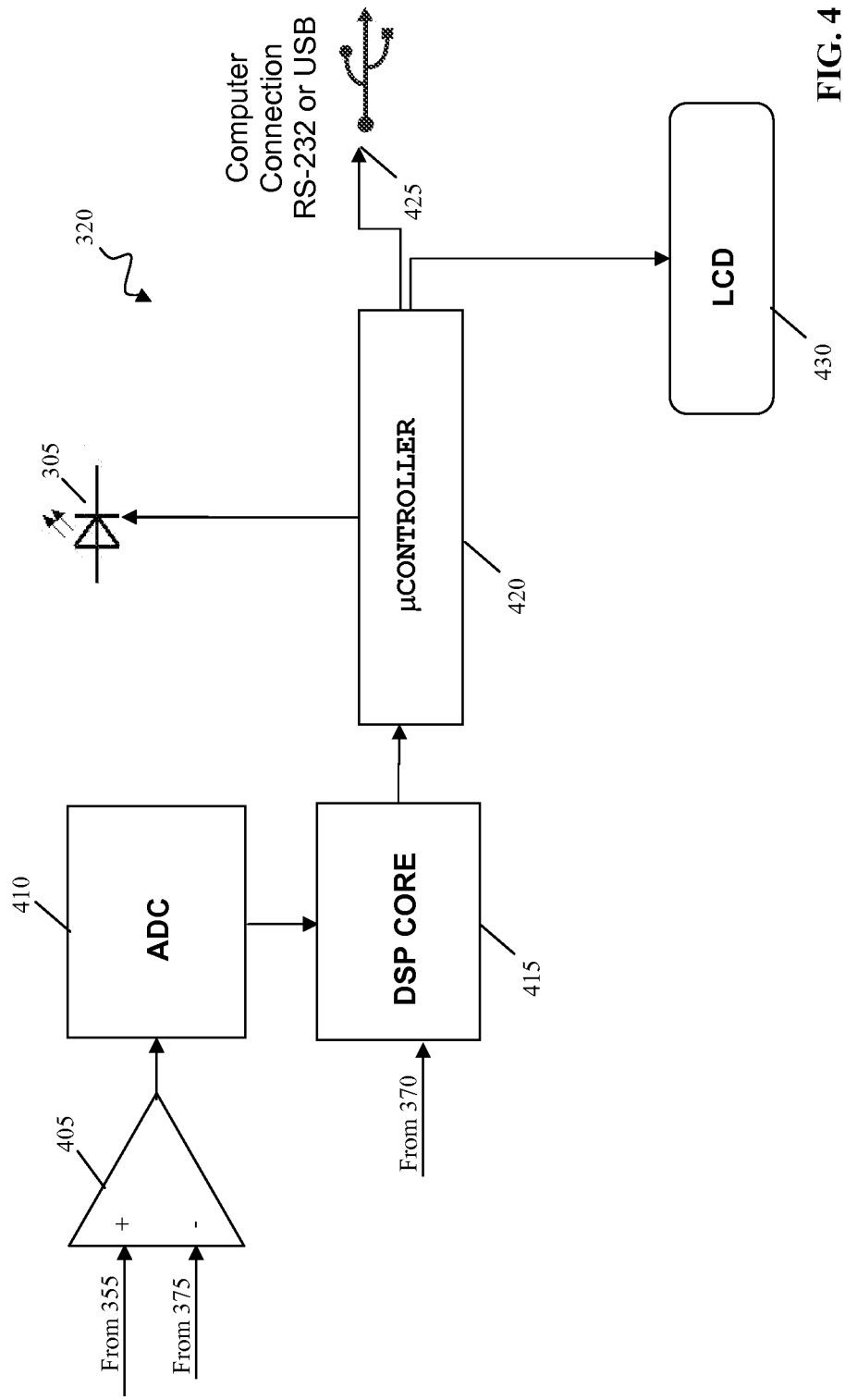
FIG. 4 shows one implementation of the system electronics of the gas analyzer of FIG. 3.

FIG. 4 shows one implementation of system electronics 320 in more detail. The illustrated implementation of system electronics 320 includes analog noise cancellation circuitry 405, an analog-to-digital converter 410, digital signal processing circuitry 415, controller circuitry 420, and one or more input/output devices 425, 430.

Analog noise cancellation circuitry 405 is circuitry for removing noise from the analog measurement signals output by transducers 355, 375. Noise cancellation circuitry 405 may include a differential amplifier, as shown. In other implementations, noise cancellation circuitry 405 may include other analog signal processing circuitry, including high, low, or band pass filters. In some implementations, analog noise cancellation circuitry 405 may also include an amplifier, such as a pass band or a lock-in amplifier. In some implementations, all or a part of analog noise cancellation circuitry 405 may be physically housed with transducers 355, 375.

Analog-to-digital converter 410 is a device for converting an analog signal, such as a noise-may celled signal output from noise cancellation circuitry 405, into one or more digital signals. In some implementations, analog-to-digital converter 410 may have multiple channels and be a relatively high speed/high resolution device. For example, analog-to-digital converter 410 may operate at sample frequency of 100 kHz and 20 bits.

Digital signal processing circuitry 415 is a device for processing one or more digital signals to improve the representation of the properties of an analyzed gaseous sample by the digital signals. For example, digital signal processing circuitry 415 may perform one or more adaptive noise cancellation algorithms to improve the signal-to-noise ratio of the digital signal output by analog-to-digital converter 410. Examples of such algorithms include a least mean squares (LMS) algorithms, normalized LMS (NLMS) algorithms, recursive least squares (RLS) algorithms, and affine projection algorithms (APA). As yet further examples, digital signal processing circuitry 415 may include digital filtering and/or amplification circuitry, including integrators and the like.

In some implementations, digital signal processing circuitry 415 may improve the representation of the properties of an analyzed gaseous sample based at least in part on the results of on one more measurements of the properties of the gaseous sample, such as temperature and/or pressure measurements made by one or more sensors 370.

Controller circuitry 420 is a device for controlling the analysis of gaseous samples by a gas analyzer. Controller circuitry 420 may be a data processing device that performs such operations by processing data in accordance with the logic of a set of machine-readable instructions. The instructions may be tangibly embodied, e.g., in hardware, in software, or in combinations thereof. The control activities may include, e.g., commencing analysis, changing analysis parameters, controlling the movement, temperature, and pressure of gas in analysis and/or references chambers, and the like.

In some implementations, controller circuitry 420 may also generate one or more measurement results. The measurement results may be raw data or processed data. Raw measurement data includes data that represents the immediate results of measurements, such as absorption coefficients at various wavelengths. Processed measurement data may include, e.g., a quantification of the concentration of one or more component species of a gas sample, correlations between the component gas species concentrations and the heath of an individual, a comparison between raw data and known gases, and indications that specific disease states may be present. As discussed above, however, processed measurement results may be generated elsewhere, e.g., in a data analyzer 120 (FIG. 1).

In some implementations, the results of data analysis may be used in controlling the analysis of gaseous samples by a gas analyzer. For example, wavelengths may be selected for analysis based on the results of measurements made on other wavelengths, or data collection parameters (e.g., collection time) may be changed based on other measurement results.

Input/output devices 425, 430 are one or more devices for interacting with a human directly and/or indirectly. Direct interaction with a human results when information is exchanged directly between the human and system electronics 320, such as when system electronics 320 outputs raw measurement results or a signal indicating that analysis is complete over an liquid crystal display (LCD) screen 430. Indirect interaction with a human results when information is presented to a second device that exchanges information with a human, such as when system electronics 320 receives changes to analysis parameters from a computer over a data port such as a RS-232 port or a USB port 425, as shown. The interaction with a human over input/output devices 425, 430 may thus involve the control of analysis by a gas analyzer 115 and/or the presentation of measurement results obtained by a gas analyzer 115.

As discussed previously, raw measurement results may include data that represents absorption coefficients at various wavelengths. The raw measurement data may include a continuous spectrum of measurements or a collection of measurements at discrete wavelengths. Raw absorption measurements may be analyzed as a linear addition of the products of absorption coefficients and concentrations of various gases, and the concentrations of the various gases may be determined.

Figure 5:
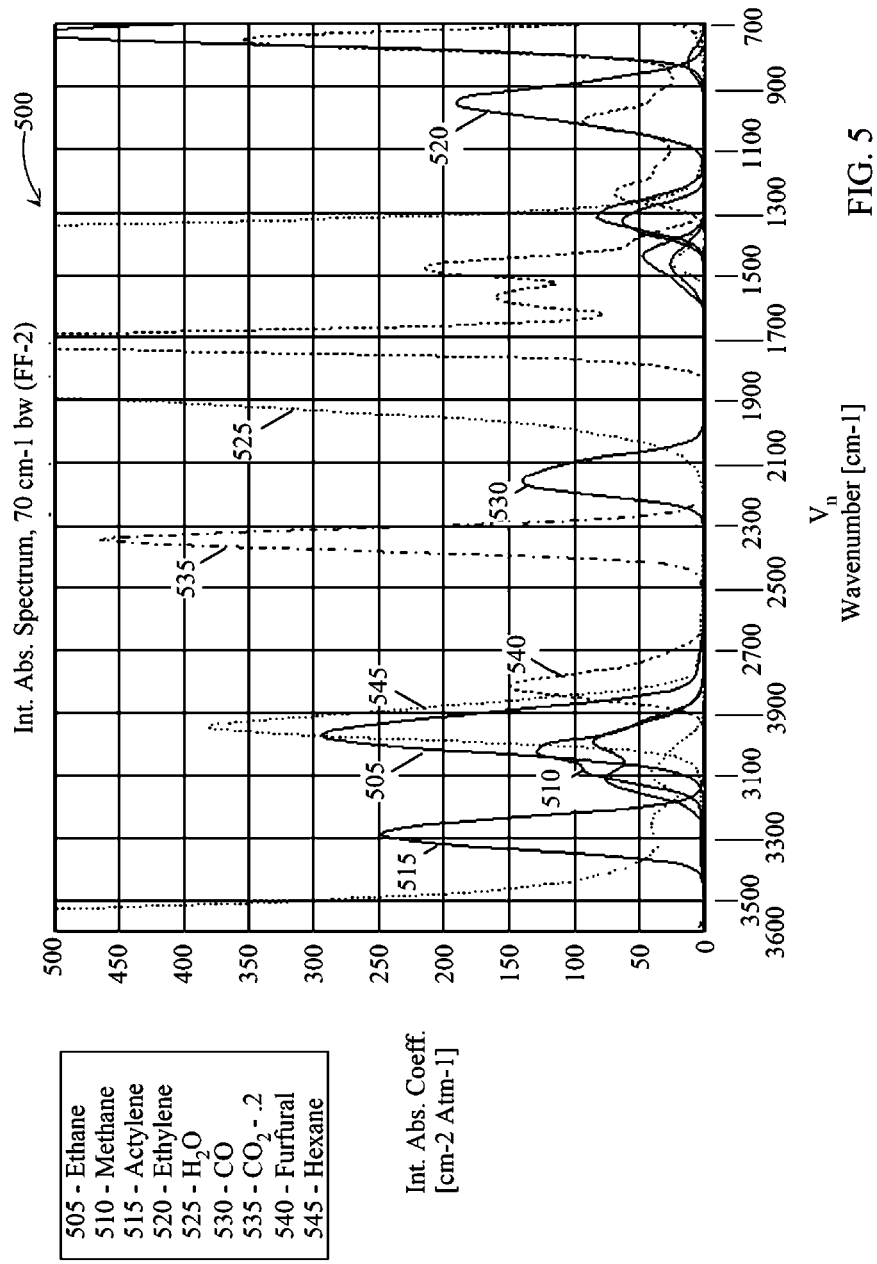
FIG. 5 is a graph of the infrared (IR) absorption spectra of various gases at a concentration of one atmosphere.

FIG. 5 is a graph 500 of the infrared (IR) absorption spectra of various example gases at a concentration of one atmosphere. Graph 500 includes an IR absorption spectrum of ethane 505, an IR absorption spectrum of methane 510, an IR absorption spectrum of acetylene 515, an IR absorption spectrum of ethylene 520, an IR absorption spectrum of water 525, an IR absorption spectrum of carbon monoxide 530, an IR absorption spectrum of carbon dioxide 535, an IR absorption spectrum of furfural 540, and an IR absorption spectrum of hexane 545. As may be seen, there is some overlap between the spectral fingerprints of spectra 505, 510, 515, 520, 525, 530, 535, 540, 545. However, there are enough unique regions to permit accurate measurements, even if an analysis sample includes a variety of gases.

As discussed above, the concentrations of the various gases may be determined either as part of the data processing activities at gas analyzer 115 or the data processing activities at data analyzer 120. Regardless of where the concentration determination is made, the concentration measurement may be used to characterize a medical condition of an individual.

Figure 6:
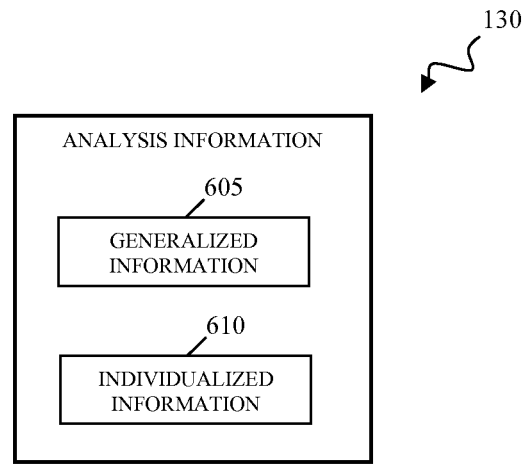
FIG. 6 is a schematic representation of analysis information that may be used in conjunction with concentration measurement results to characterize a medical parameter.

FIG. 6 is a schematic representation of analysis information 130 that may be used in conjunction with concentration measurement results to characterize a medical condition of an individual. Analysis information 130 includes generalized information 605 and personalized information 610. Generalized information 605 reflects the correlation between the characteristics of gaseous samples associated with a population of individuals and a medical condition of that population. For example, generalized information 605 may reflect the correlation between the concentration of gaseous species in gaseous samples drawn from a population and a disease state in that population. The population of individuals may be humanity as a whole or a subgroup of a humanity that shares common characteristics. For example, the common characteristics may include demographic and physical characteristics (e.g., age, race, gender, weight, height, activity level, and the like), health conditions (e.g., specific disease states, pregnancy, or the like), and/or characteristics of the environment of the individuals (e.g., diet, medication, altitude, and the like). In some implementations, generalized information 605 may be dynamically updated to reflect a changed disposition of the analyzed individual relative to these characteristics. For example, as an individual ages or changes diet, generalized information 605 may be changed to reflect such changes.

Individualized information 610 reflects the correlation between the characteristics of a gaseous sample associated with a specific individual and a medical condition of that specific individual. For example, individualized information 610 may reflect the correlation between the concentration of gaseous species in a gaseous sample drawn from a specific individual and a disease state. Individualized information 610 may be based on a historical record of the results of analysis of a gaseous sample associated with the specific individual. Thus, in some implementations, individualized information 610 may be dynamically changeable to reflect an updated understanding of the personal characteristics of an individual, e.g., as an additional historical record is accumulated.

Figure 7:
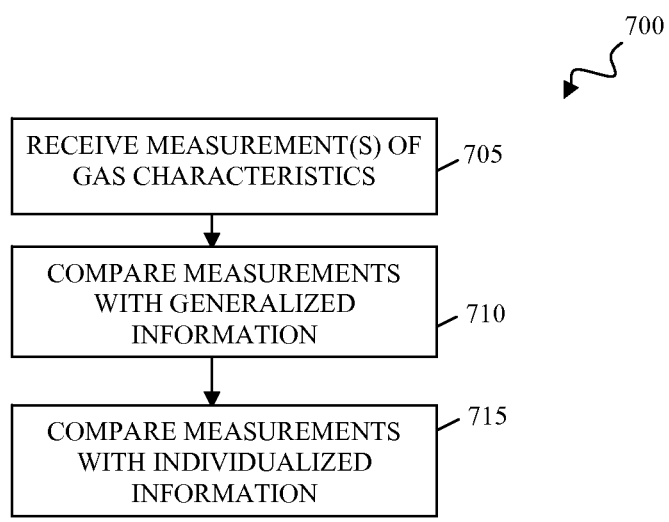
FIG. 7 is a flowchart of a process for the medical analysis of gases.

FIG. 7 is a flowchart of a process 700 for the analysis of gases, such as for medical purposes. Process 700 may be performed by a data processing device that performs data processing activities in accordance with the logic of a set of machine-readable instructions. For example, a process 700 may be performed by data analyzer 120 in system 100 (FIG. 1).

The system performing process 700 may receive the results of one or more measurements performed on a gaseous sample at 705. The results may reflect a gaseous sample's physical, optical, and/or chemical properties. For example, the results may reflect the optical properties of a gaseous sample, such as those obtained using photo-acoustic spectroscopy. The measurement information may thus reflect the concentration of various species in a gaseous sample.

The system performing process 700 may compare the received measurement results with generalized information at 710. The comparison may be performed for medical purposes, such as the determination of a likelihood that one or more disease states is present in an individual associated with the gaseous sample.

The system performing process 700 may compare the received measurement results with individualized information at 715. The comparison may be performed for medical purposes, such as the determination of a likelihood that one or more disease states is present in an individual associated with the gaseous sample, to monitor the progression of a disease state over time, and/or to monitor the efficacy of a treatment regimen.

In some implementations, the comparison with generalized information at 710 may occur months before the comparison with the individualized information at 715. For example, comparisons with generalized information may be made until a statistically useful database for a specific individual has been assembled. Once such a database has been assembled, the comparison with the individualized information may be performed.

In some implementations, the results of the comparison with generalized information at 710 and the results of the comparison with the individualized information at 715 may be used together to determine a single parameter. For example, both comparison results may be used to determine the likelihood that a disease state is present in an individual.

Figures 8, 9:
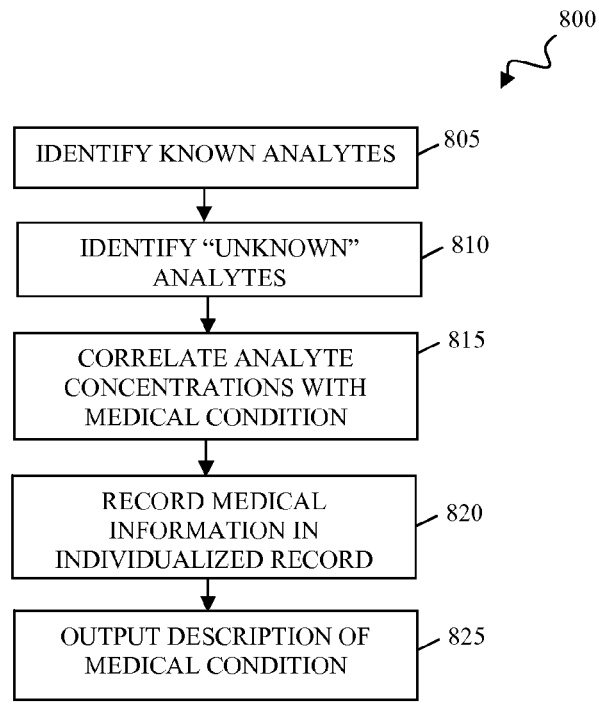
FIG. 8 is a flowchart of a process for the medical analysis of gases.
FIG. 9 is a schematic representation of a data assembly that records individualized medical information.

FIG. 8 is a flowchart of a process 800 for the medical analysis of gases. Process 800 may be performed by a data processing device that performs data processing activities in accordance with the logic of a set of machine-readable instructions. For example, a process 800 may be performed by data analyzer 120 in system 100 (FIG. 1).

As discussed further below, process 800 includes a comparison of received measurement results with generalized information and a comparison of received measurement results with individualized information. Process 800 may thus be performed in conjunction with process 700 (FIG. 7). Process 800 may also be performed in isolation.

The system performing process 800 may identify whether any "known" analytes are present in a gaseous sample at 805. Known analytes are those that a data processing system expects to be present in a gaseous sample. Such expectation may be reflected in the algorithm or other data analyzed used by the data processing system to analyze raw measurement results.

The identification of known analytes may include comparing IR absorption measurements with IR absorption coefficients to determine the concentration(s) of one or more components. For example, formaldehyde has two absorption regions around 3.56 microns (C—H bonds) and 5.64-5.82 microns (C=O bond). Formaldehyde thus has some cross-sensitivity to methane (which has an absorption region around 3.39 microns), acetaldehyde, methanol (which has an absorption region around 3.3-3.5 microns, dimethyl ether (which has an absorption region around 3.4-3.5 microns), and water (which has an absorption region around 5-6 microns). Carbon monoxide, carbon dioxide, ethane, ethylene, acetylene are not cross-sensitive to formaldehyde. Thus, one water is removed from a gaseous sample, absorption in the 5.6-5.8 micron region may be used to detect formaldehyde.

The system performing process 800 may also identify if any "unknown" analytes are present in a gaseous sample at 810. Unknown analytes are those that a data processing system does not expect to be present in a gaseous sample. The identification of unknown analytes may include subtracting the impact of known components from raw measurement results. For example, IR absorption attributable to known components may be subtracted from raw measurement results to generate a set of unattributed IR absorption. The unattributed IR absorption may then be compared to additional IR spectra to identify unknowns. In some implementations, information regarding such unknowns (such as IR absorption coefficients) may be used in subsequent identifications of known analytes for the associated individual.

The system performing process 800 may correlate the concentrations of known analytes and unknown analytes with the medical condition of an individual at 815. The medical condition may include the likelihood of a disease state being present, the severity of any such disease state, the efficacy of any treatment protocol, and the like. The correlations may include monitoring changes in analyte concentrations for an individual over time and comparing such analyte concentrations with generally acceptable levels of the analytes. The comparisons may determine, e.g., if a set of concentration measurements are within acceptable levels for individuals of a certain demographic group, having certain physical characteristics, having certain medical conditions, subject to certain environmental conditions, and the like. The correlations may thus identify one or more disease states based on analyte concentrations, generalized information, and/or individualized information.

The system performing process 800 may record medical information in an individualized record at 820. The medical information may include raw measurement results, the results of analyte identifications, the results of correlations of analytes with medical conditions, and the like. Such individualized records may themselves be used in subsequent analyses of gases. For example, personalized medical information for a single individual may be recorded on a daily or other basis. Changes relative to this individualized baseline may be recorded and used to identify medical conditions. If a device is subsequently used by a different individual, the device may be recalibrated to generalized settings. Thus, the device may be used for multiple individuals or as an individualized monitor for a single individual.

The system performing process 800 may output a description of the medical condition of an individual at 825. The description may include, e.g., raw measurement results, analyte identifications, identifications of any disease states, or the like. For example, the description may include a simple yes/no output indicating whether or not the individual is likely to have a certain disease. The medical condition description may be output over one or more output devices, such as input/output devices 425, 430 (FIG. 4).

FIG. 9 is a schematic representation of one implementation of a data assembly 900 that records individualized medical information 610 (FIG. 6) related to the analysis of gases. Data assembly 900 may thus be populated at 825 and accessed at 815 in process 800 (FIG. 8).

Data assembly 900 is shown as a data table, although other classes of data assemblies (e.g., records, lists, arrays, objects, files, documents, and the like) are possible. Data assembly 900 includes an identifier 905 of an individual, a component column 910, and one or more characteristic columns 915, 920. Identifier 905 identifies an individual with whom data assembly 900 is associated. Identifier 905 may identify the individual, e.g., by name, by number, or otherwise. Component column 910 includes information that identifies potential component species, or groups of component species, of a gaseous sample associated with the individual. Component column 910 may identify potential component species or component species groups, e.g., by name, by number, or otherwise.

Characteristic columns 915, 920 include information that describes one or more characteristics of the component species identified in component column 910 for the individual identified by identifier 905. For example, characteristic columns 915, 920 may include measurement results (such as concentration), measurement information (such as, e.g., time and date of measurement, measurement parameters, and the like), and additional information thought to be relevant to the medical analysis of gases. The additional information may include, e.g., dietary information, medication information, activity level information, and the like.

The contents of columns 910, 915, 920 are associated in a collection of rows 925 so that the information describing component species is associated with information describing the characteristics of those component species.

In some implementations, the information in data assembly 900 may be stored in association with other medical information. The other medical information may include descriptions of the medical condition of an individual that are obtained by other means, i.e., means other than the analysis of a gas sample associated with the individual. For example, the time since conception or severity of disease state may be recorded in association with the gas analysis information in data assembly 900.

Table 1 lists example groups of component species that may be identified in component column 910. As discussed above, for the individual identified by identifier 905, data assembly 900 may store information describing the characteristics of these groups of component species (such as concentration) in association with information identifying these groups of component species.

TABLE 1

| Group classification |
|---|
| Non-aromatic hydrocarbons |
| Non-aromatic halogenated hydrocarbons |
| Non-aromatic alcohols |
| Non-aromatic mercaptans and sulphides |
| Non-aromatic amines |
| Non-aromatic nitro and nitroso |
| Non-aromatic ketones |
| Non-aromatic aldehydes |
| Non-aromatic carboxylic acids |
| Non-aromatic esters and lactones |
| Non-aromatic amides |
| Non-aromatic nitriles and cumulated double bonds |
| Non-aromatic ethers, acetals, and epoxides |
| Non-aromatic sulphane-oxygen compounds |
| Alkynes |
| Aromatic hydrocarbons |
| Aromatic halogenated hydrocarbons |
| Aromatic alcohol and phenols |
| Aromatic mercaptans and sulphides |
| Aromatic amines |
| Aromatic nitro and nitroso |
| Aromatic ketones |
| Aromatic aldehydes |
| Aromatic carboxylic acids |
| Aromatic esters and lactones |
| Aromatic amino acids and salts |
| Aromatic nitriles and cumulated double bonds |
| 5-membered aromatic heterocycles |
| 6-membered aromatic heterocycles |
| 5-membered fused aromatic heterocycles |

Table 2 lists example component species that may be identified in component column 910. As discussed above, for the individual identified by identifier 905, data assembly 900 may store information describing the characteristics of these component species (such as concentration) in association with information identifying these component species.

TABLE 2

| BTC |
|---|
| Acetonitrile |
| Benzonitrile |
| Nitrous oxide |
| Cabron monoxide |
| Hydrogen sulphide |
| Ammonia |
| Water |
| Carbon disulphide |
| Dimethyl sulphoxide |
| Benzene |

Figure 10:
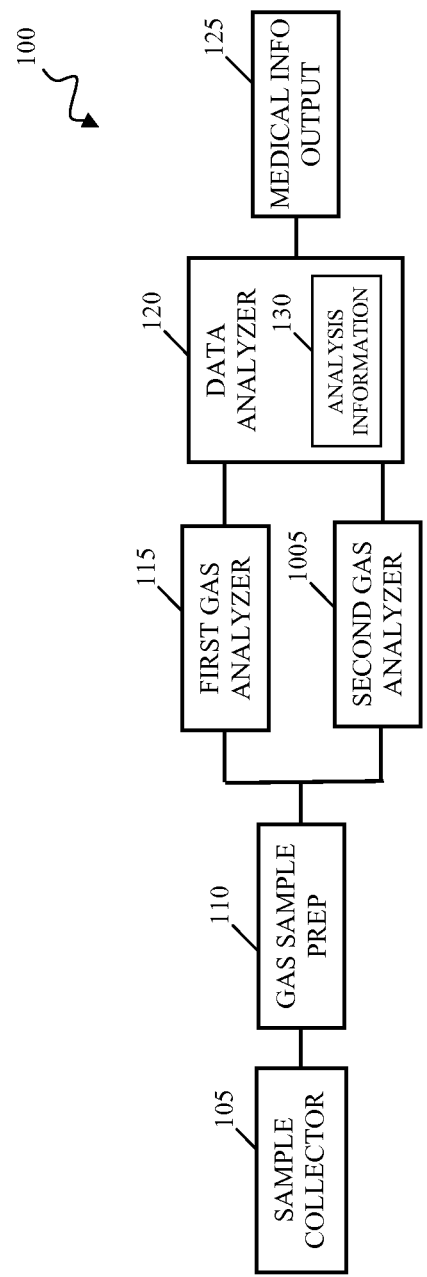
FIG. 10 is a schematic representation of a system for the analysis of gases in accordance with an alternate implementation of the invention.

FIG. 10 is a schematic representation of an alternative implementation of system 100 for the analysis of gases, such as for medical purposes. In addition to sample collector 105, gas sample preparation device 110, a first gas analyzer 115, data analyzer 120, and output 125, this implementation of system 100 also includes a second gas analyzer 1005.

Second gas analyzer 1005 is a device for analyzing a gaseous sample prepared by gas sample preparation device 110 to generate one or more signals that characterize the gaseous sample. Gas analyzer 1005 may analyze a gaseous sample by measuring one or more characteristics of the gaseous sample, including the sample's physical, optical, and chemical properties. For example, gas analyzer 1005 may include a conductometric sensor, such as the hydrogen sensor described in U.S. Patent Publication Ser. No. 2004/0261500 (filed May 26, 2004), the contents of which are incorporated herein by reference. This conductometric sensor operates through the detection of conductivity changes of a collection of palladium nanoparticles.

In some implementations, gas analyzer 1005 may also include one or more data outputs and inputs for exchanging information with other components of system 100. For example, gas analyzer 1005 may include a measurement output that outputs measurement information characterizing a gas sample. Note that such measurement information may be output to multiple components in system 100, including first gas analyzer 115.

Measurement information output to components in system 100 may be treated by those components similarly to the measurement information output from first gas analyzer 115.

The systems and techniques described herein may be used in a number of different scenarios. For example, the systems and techniques may be used to identify:

Uremic breath. Uremic breath is associated with renal insufficiency, poor dental health, and/or gastrointestinal problems. Toxic volatile metabolites may be identified, including dimethylamine and trimethylamine. See, e.g., the information available on the Internet at the webpage with the URL of content.nejm.org/cgi/content/abstact/297/0/132.

H. pylory test: A positive test for H. pylori indicates that the gastrointestinal pain may be caused by bacteria. For example, *Helicobacter pylori* produce a urease enzyme, the detection of which forms the basis of an isotope tracer test known as the urea breath test. See, e.g., the information available on the Internet at the webpage with the URL of labtestsonline.org/understanding/analytes/h_pylori/test.html.

Pancreatic insufficiency: It has been suggested that bacterial overgrowth in patients with exocrine pancreatic insufficiency may be identified using a hydrogen breath test with glucose. See, e.g., the information available on the Internet at the webpage of ncbi.nlm.nih.gov/entrez/query.fcgi?cmd=Retrieve&db=pubmed&dopt=Abstract&list_uids=9598808&itool=iconabstr&query_hl=2.

Asthma: A decrease in exhaled nitric oxide concentration suggests that the anti-inflammatory treatment may be decreasing the lung inflammation associated with asthma. Studies show that nitric oxide levels above 30 parts per billion correlate with moderate to severe asthma. See, e.g., the information available on the Inteternet at the webpage with the URL of labtestsonline.org/news/fdaasthma030509.html.

Ethane concentrations: Ethane concentrations in breath may correlate with the severity of oxidant stress and metabolic disturbances. Ethane concentrations may also correlate with pathological conditions in patients on long-term hemodialysis. See, e.g., the information available on the Internet at the webpage with the URL of ncbi.nlm.nih.gov/entrez/query.fcgi?cmd=Retrieve&db=PubMed&list_uids=12826252&dopt=Abstract.

Lipid Peroxidation: Lipid peroxidation may increase concentrations of ethylene, ethane, and pentane in exhaled air. See, e.g., the information available on the Internet at the webpage with the URL of tracegasfac.science.ru.nl/respirat1.htm.

Lung Cancer: Increased concentrations (on the order of 1-5 ppm) of the following may be positively correlated with lung cancer: acetone, acetophenone, nitric oxide (NO), propenal, phenol, benzaldehyde, 2-butanone, ethylpropanoate, methylisobutenoate, and nonanal.

Correlations between volatile species and health disorders: Various volatile chemical species are associated with different disorders. Diagnosis of such disorders may be possible when such species are identified. Table 3 lists examples of such associations.

TABLE 3

| Sample/Disorder | Volatile compound |
|---|---|
| Human breath, urine | VOCs |
| Aerobic Gram (−) bacteria | VOCs |
| Intraperitoneal fluid | VOCs |
| Anaerobic infections | Acetic, butyric acid |
| Human pus, purulent fluids | Isobutyric, isovaleric, and isocaproic |
| Urine/metabolic disorders | Isovaleric acid |
| Blood plasma, CSF | 3-methylbutanal |
| Alveolar air/hepatic coma | Methyl-mercaptan |
| Alveolar air/schizophrenia | Pentane |
| Alveolar air/ketosis | Acetone |
| Cardiopulmonary disease | Acetone and ethanol |

A number of implementations have been described. Nevertheless, it will be understood that various modifications may be made. For example, many of the described systems and techniques may be used for environmental monitoring. Such environmental monitoring can be performed in closed environments, such as submarines or the cockpit of an airplane. Such environmental monitoring can include the detection of environmental contaminants, such as those to which OSHA restricts exposure. Examples of such contaminants include carbon monoxide, carbon dioxide, nitrogen dioxide, alkanes, aromatics, and water. Process activities may be performed in different order or omitted and yet meaningful results can still be achieved. System components may be omitted and/or modified and yet useful function can be retained. Accordingly, other implementations are within the scope of the following claims.

What is claimed is:

1. A method comprising:
   using photoacoustic spectroscopy to determine data describing infrared absorption at a collection of wavelengths of a gas sample taken from an individual;
   based on the data describing the infrared absorption, determining measurements of concentrations of a plurality of different non-aqueous species in the gas sample taken from the individual;
   receiving, by a data processing device, the measurements of concentrations of the plurality of different non-aqueous species in the gas sample taken from the individual;
   correlating, by the data processing device, the concentration measurements with a medical condition of the individual; and
   making a result of the correlation available over an output device of the data processing device,
   wherein analysis information is used, by the data processing device, in conjunction with concentration measurement results to characterize a medical condition of the individual, the analysis information including generalized information, the generalized information reflecting a correlation between concentrations of the non-aqueous species in gas samples associated with a population of individuals and a medical condition of the population,
   wherein the concentrations of the non-aqueous species in gas samples is compared, by the data processing device, with the generalized information until sufficient gas samples have been taken and analyzed to assemble a statistically useful database of individualized information for a given individual, and comparing the concentrations of the non-aqueous species also with the individualized information once such a database has been assembled.

2. The method of claim 1, wherein the correlating the concentration measurements with the medical condition of the individual is further based on a historical record of previously received concentration measurements of at least one of the plurality of different non-aqueous species in gas samples taken from the individual over a period of time at least longer than twenty-four hours.

3. The method of claim 2, further comprising:
   supplementing the historical record with information describing the concentration measurements; and
   correlating a subsequent concentration measurement with the medical condition based on the supplemented historical record.

4. The method of claim 3, wherein the subsequent concentration measurement is taken from the individual one or more months later than the concentration measurements of the non-aqueous species in the gas sample taken from the individual.

5. The method of claim 2, wherein the historical record of the concentration of the species in gas samples associated with the individual represents one or more concentration measurements of the species in gas samples taken from the individual one or more days previous to a day when the concentration measurements of the non-aqueous species in the gas sample taken from the individual was received by the data processing system.

6. The method of claim 2, wherein the result of the correlation is a determination of an efficacy of a treatment protocol for a disease possessed by the individual, wherein the historical record includes concentration measurements of the species in gas samples previously taken from the individual one day or more earlier than a day when the concentration measurements of the non-aqueous species in the gas sample associated with the individual was received by the data processing system, wherein the individual was on the treatment protocol before at least one of the concentration measurements of the species in gas samples previously taken from the individual one day or more earlier than a day when the concentration measurements of the non-aqueous species in the gas sample associated with the individual was received by the data processing system.

7. The method of claim 2, wherein the historical record includes a determination of a baseline medical condition of the individual to which the result of the correlation is compared.

8. The method of claim 1, further comprising identifying, by the data processing device, a disease state of the individual based on the concentrations of the non-aqueous species in the gas sample and the generalized information.

9. The method of claim 1, wherein using photoacoustic spectroscopy comprises:
   generating infrared electromagnetic radiation;
   interacting the gas sample with the infrared electromagnetic radiation;
   varying incidence of the infrared electromagnetic radiation on the gas sample; and
   transducing consequences of time varying interaction between the incident infrared electromagnetic radiation and the gas sample.

10. The method of claim 1, wherein the result of the correlation is a determination that the individual has a specified disease.

11. The method of claim 1, wherein the result of the correlation is a diagnosis that the individual has a specified disease not previously identified in the individual.

12. A method comprising:
    measuring infrared absorption of a first gas sample associated with an individual using photoacoustic spectroscopy;
    receiving, by a data processing device, data representing the infrared absorption of the first gas sample associated with the individual;
    correlating, by the data processing device, the data representing the infrared absorption of the first gas sample with a medical condition of the individual based on generalized information reflecting a correlation between characteristics of gas samples associated with a population of individuals and a medical condition of the population;
    adding, by the data processing device, information describing the infrared absorption to a collection of individualized information reflecting a correlation between characteristics of gas samples associated with the individual and a medical condition of the individual;
    measuring infrared absorption of a second gas sample associated with the individual using photoacoustic spectroscopy;
    receiving, by the data processing device, data representing the infrared absorption of the second gas sample associated with the individual; and
    subsequently correlating, by the data processing device, the data representing the infrared absorption of the second gas sample with a medical condition of the individual based on the collection of individualized information,
    wherein analysis information is used, by the data processing device, in conjunction with concentration measurement results to characterize a medical condition of the individual, the analysis information including generalized information, the generalized information reflecting a correlation between concentrations of non-aqueous species in gas samples associated with a population of individuals and a medical condition of the population, wherein the concentrations of the non-aqueous species in gas samples is compared, by the data processing device, with the generalized information until sufficient gas samples have been taken and analyzed to assemble a statistically useful database of individualized information for a given individual, and comparing the concentrations of the non-aqueous species also with the individualized information once such a database has been assembled.

13. The method of claim 12, wherein the receiving the data representing the infrared absorption of the first gas sample further comprises receiving, by the data processing device, a concentration of a breath trace compound.

14. The method of claim 12, wherein a result of the correlation is a diagnosis that the individual has a specified disease not previously identified in the individual.

15. The method of claim 12, wherein using photoacoustic spectroscopy comprises:
   generating infrared electromagnetic radiation;
   interacting the gas sample with the infrared electromagnetic radiation;
   varying incidence of the infrared electromagnetic radiation on the gas sample; and
   transducing consequences of time varying interaction between the incident infrared electromagnetic radiation and the gas sample.

16. A method implemented in a data processing system, comprising:
   using photoacoustic spectroscopy to determine data describing infrared absorption at a collection of wavelengths of a gas sample taken from an individual;
   based on the data describing the infrared absorption, determining measurements of concentrations of a non-aqueous species in the gas sample taken from the individual;
   receiving, by the a data processing system, the measurements of concentrations of the non-aqueous species in the gas sample taken from the individual;
   correlating, by the data processing system, the concentration measurements with a medical condition of the individual; and
   making a result of the correlation available over an output device of the data processing system,
   wherein analysis information is used in conjunction with concentration measurement results to characterize a medical condition of the individual, the analysis information including generalized information, the generalized information reflecting a correlation between concentrations of the non-aqueous species in gas samples associated with a population of individuals and a medical condition of the population, the method further comprising identifying, by the data processing system, a disease state of the individual based on the concentration of the non-aqueous species in the gas sample and the generalized information,
   wherein the concentrations concentration of the non-aqueous species in gas samples is compared with the generalized information until sufficient gas samples have been taken and analyzed to assemble a statistically useful database of individualized information for a given individual, and comparing the concentrations of the non-aqueous species also with the individualized information once such a database has been assembled.

17. The method of claim 16, wherein the correlating the concentration measurements with the medical condition of the individual is further based on a historical record of previously received concentration measurements of at least one of a plurality of non-aqueous species in gas samples taken from the individual over a period of time at least longer than twenty-four hours.

18. The method of claim 17, further comprising:
   supplementing, by the data processing system, the historical record with information describing the concentration measurements; and
   correlating, by the data processing system, a subsequent concentration measurement with the medical condition based on the supplemented historical record.

19. The method of claim 18, wherein the subsequent concentration measurement is taken from the individual one or more months later than the concentration measurements of the non-aqueous species in the gas sample taken from the individual.

20. The method of claim 17, wherein the historical record of the concentration of the species in gas samples associated with the individual represents one or more concentration measurements of the species in gas samples taken from the individual one or more days previous to a day when the concentration measurements of the non-aqueous species in the gas sample taken from the individual was received by the data processing system.

21. The method of claim 16, wherein the result of the correlation is a diagnosis that the individual has a specified disease not previously identified in the individual.

22. The method of claim 16, wherein using photoacoustic spectroscopy comprises:
   generating infrared electromagnetic radiation;
   interacting the gas sample with the infrared electromagnetic radiation;
   varying incidence of the infrared electromagnetic radiation on the gas sample; and
   transducing consequences of time varying interaction between the incident infrared electromagnetic radiation and the gas sample.

* * * * *